(12) United States Patent
Nelson et al.

(10) Patent No.: US 7,058,453 B2
(45) Date of Patent: Jun. 6, 2006

(54) APPARATUS AND METHOD FOR REMOTE THERAPY AND DIAGNOSIS IN MEDICAL DEVICES VIA INTERFACE SYSTEMS

(75) Inventors: Chester Gary Nelson, Plymouth, MN (US); Michael Thomas Lee, Minnetonka, MN (US); Michael G. Schrenk, Richfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 695 days.

(21) Appl. No.: 10/068,478

(22) Filed: Feb. 7, 2002

(65) Prior Publication Data

US 2002/0072785 A1 Jun. 13, 2002

Related U.S. Application Data

(62) Division of application No. 09/460,580, filed on Dec. 14, 1999, now Pat. No. 6,418,346.

(51) Int. Cl.
*A61N 1/372* (2006.01)

(52) U.S. Cl. .............................. 607/60; 607/32; 607/59
(58) Field of Classification Search ............. 607/30–32, 607/59, 60
See application file for complete search history.

(56) References Cited

U.S. PATENT DOCUMENTS

| | | | |
|---|---|---|---|
| 3,943,918 A | 3/1976 | Lewis | |
| 4,319,241 A | 3/1982 | Mount | |
| 4,494,950 A | 1/1985 | Fischell | |
| 4,886,064 A | 12/1989 | Strandberg | |
| 4,987,897 A | 1/1991 | Funke | |
| 5,311,449 A | 5/1994 | Adams | |
| 5,345,362 A | 9/1994 | Winkler | |
| 5,441,047 A | 8/1995 | David et al. | |
| 5,701,904 A | 12/1997 | Simmons et al. | |
| 5,716,384 A | 2/1998 | Snell | |
| 5,720,770 A | 2/1998 | Nappholz et al. | |
| 5,724,985 A | 3/1998 | Snell et al. | |
| 5,752,976 A | 5/1998 | Duffin et al. | |
| 5,772,586 A | 6/1998 | Heinonen et al. | |
| 5,840,020 A | 11/1998 | Heinonen et al. | |
| 5,941,829 A | 8/1999 | Saltzstein et al. | |
| 6,168,563 B1 | 1/2001 | Brown | |
| 6,249,705 B1 * | 6/2001 | Snell | 607/59 |

FOREIGN PATENT DOCUMENTS

| | | |
|---|---|---|
| CA | 1131315 | 9/1982 |
| WO | WO 99/14882 | 3/1999 |

* cited by examiner

*Primary Examiner*—George R. Evanisko
(74) *Attorney, Agent, or Firm*—Daniel G. Chapik; Girma Wolde-Michael

(57) ABSTRACT

A system for transferring data into and out of medical devices wherein a personal data manager (PDM) is used in a web-based network is disclosed. The PDM co-operates with a programmer to enhance remote monitoring of implanted medical devices on a chronic basis to deliver clinical therapy in real time. The PDM is handheldable and mobile and expands the reach of the programmer by storing and forwarding data from the programmer to web-based network constituting a medical environment. The PDM is also implemented to store and forward information to PCs and similar peripheral equipment. In a specialized application, the PDM is configured to exchange data with the unregulated operational/functional segments of the IMD.

17 Claims, 5 Drawing Sheets

APPARATUS AND METHOD FOR REMOTE THERAPY AND DIAGNOSIS IN MEDICAL DEVICES VIA INTERFACE SYSTEMS

This application is a divisional of application Ser. No. 09/460,580, filed Dec. 14, 1999 U.S. Pat. No. 6,418,346.

THE FIELD OF THE INVENTION

The present invention relates to medical device systems. Specifically, the invention pertains to a remote bi-directional communications with one or more programmers and medical units, or related controls that are associated with implantable medical devices (IMDs). More specifically, the invention relates to a handheld or external, independent device implemented in an integrated system and method of bi-directional telecommunications between a web-based expert data center and a programmer, utilizing various types of network platforms and architecture, to implement in the IMDs, chronic monitoring, therapeutic and diagnostic procedures and data exchange remotely.

BACKGROUND OF THE INVENTION

A technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide a seamless system of remote patient diagnostics, care and medical services in a time and place independent manner.

Prior art methods of clinical services are generally limited in operations. For example, if a physician needs to review the performance parameters of an implantable device in a patient, it is likely that the patient has to go to the clinic. Further, if the medical conditions of a patient with an implantable device warrant a continuous monitoring or adjustment of the device, the patient would have to stay in a hospital indefinitely. Specifically, patient conditions which require chronic monitoring of the IMD present serious economic problems in the management of therapy and diagnosis on a continuous basis. Under the exemplary scenario, as the segment of the population with implanted medical devices increases, many more hospitals/clinics including service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the prior art practice requires that a patient visit a clinic center for occasional retrieval of data from the implanted device to assess the operations of the device and gather patient history for both clinical and research purposes. Such data is acquired by having the patient in a hospital/clinic to down load the stored data from the implantable medical device. Depending on the frequency of data collection this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed. Further, in medical practice it is an industry-wide standard to keep an accurate record of past and temporaneous procedures relating to an IMD uplink with, for example, a programmer. It is required that the report contain the identification of all the medical devices involved in any interactive procedure. Specifically, all peripheral and major devices that are used in down linking to the IMD need to be reported. Currently, such procedures are manually reported and require an operator or a medical person to diligently enter data during each procedure. One of the limitations of the problems with the reporting procedures is the fact that it is error prone and requires rechecking of the data to verify accuracy.

A further limitation of the prior art relates to the management of multiple medical devices in a single patient. Advances in modern patient therapy and treatment have made it possible to implant a number of devices in a patient. For example, IMDs such as a defibrillator or a pacer, a neural implant, a drug pump, a separate physiologic monitor and various other IMDs may be implanted in a single patient. To successfully manage the operations and assess the performance of each device in a patient with multi-implants requires a continuous update and monitoring of the devices. Further, it may be preferred to have an operable communication between the various implants to provide a coordinated clinical therapy to the patient. Thus, there is a need to monitor the IMDs including the programmer on a regular, if not a continuous, basis to ensure optimal patient care. In the absence of other alternatives, this imposes a great burden on the patient if a hospital or clinic is the only center where the necessary upgrade, follow up, evaluation and adjustment of the IMDs could be made. Further, even if feasible, the situation would require the establishment of multiple service areas or clinic centers to support the burgeoning number of multi-implant patients world-wide.

Accordingly it is vital to have a programmer and a personal data monitor (PDM) units that would connect to a remote expert data center, a remote web-based data center or a remote data center, all these terms being alternate equivalents as used herein, to provide access to the expert system and import the expertise to a local environment. Further, it is a significant advantage to have a PDM which communicates with the unregulated non-clinical sections of the IMD in addition to being communicable with the programmer and to also serve as a cost-effective mobile, handheld data transfer unit. Furthermore, it is very desirable to have a PDM system which communicates with the diagnostic section of the IMD to routinely perform diagnosis-related data exchange with the IMD. More specifically, it is highly desirable to have a PDM unit that is interactive with various peripheral communications and computer devices to promote remote delivery of patient therapy and clinical care at reasonable cost and speed.

The proliferation of patients with multi-implant medical devices worldwide has made it imperative to provide remote services to the IMDs and timely clinical care to the patient. Frequent use of programmers to communicate with the IMDs and provide various remote services, consistent with co-pending applications titled "System and Method for Transferring Information Relating to an Implantable Medical Device to a Remote Location," filed on Jul. 21, 1999, Ser. No. 09/358,081; "Apparatus and Method for Remote Troubleshooting, Maintenance and Upgrade of Implantable Device Systems," filed on Oct. 26, 1999, Ser. No. 09/426,741, now U.S. Pat. No. 6,442,433; "Tactile Feedback for Indicating Validity of Communication Link with an Implantable Medical Device," filed Oct. 29, 1999, Ser. No. 09/430,708, now U.S. Pat. No. 6,644,321; "Apparatus and Method for Automated Invoicing of Medical Device Systems" filed Oct. 29, 1999, Ser. No. 09/430,208, now U.S. Pat. No. 6,385,593; "Apparatus and Method for Remote Self- Identification of Components in Medical Device Systems," filed Oct. 29, 1999, Ser. No. 09/429,958, abandoned in favor of application filed Dec. 7, 2001, Ser. No. 10/010,406, now U.S. Pat. No. 6,754,538: "Apparatus and Method to Automate Remote Software Updates of Medical Device Systems," filed Oct. 29, 1999, Ser. No. 09/429,960, now U.S. Pat. No. 6,363,282: "Method and Apparatus to Secure Data Transfer From Medical Device Systems," filed Nov. 2, 1999, Ser. No. 09/431,881; "Implantable Medical Device Programming Apparatus Having An Auxiliary Component Storage Compartment," filed Nov. 4, 1999, Ser. No. 09/433,477, now U.S. Pat. No. 6,411,851; and "Remote Delivery Of Software-Based Training For Implantable Medical Device Systems," filed Nov. 10, 1999, Ser. No. 09/437,615, now U.S. Pat. No. 6,386,882, which are all incorporated by reference herein in their entirety, has become an important aspect of patient care. Thus, In light of the referenced disclosures, use of a PDM system as an interface mobile unit between an IMD and an expert data center is a significant advance over the prior art.

The prior art provides various types of remote sensing and communications with an implanted medical device. One such system is, for example, disclosed in Funke, U.S. Pat. No. 4,987,897 issued Jan. 29, 1991. This patent discloses a system that is at least partially implanted into a living body with a minimum of two implanted devices interconnected by a communication transmission channel. The invention further discloses wireless communications between an external medical device/programmer and the implanted devices.

One of the limitations of the system disclosed in the Funke patent includes the lack of communication between the implanted devices, including the programmer, with a remote clinical station. If, for example, any assessment, monitoring or maintenance is required to be performed on the IMD the patient will have to go to the remote clinic station or the programmer device needs to be brought to the patient's location. More significantly, the operational worthiness and integrity of the programmer cannot be evaluated remotely thus making it unreliable over time as it interacts with the IMD.

Yet another example of sensing and communications system with a plurality of interactive implantable devices is disclosed by Stranberg in U.S. Pat. No. 4,886,064, issued Dec. 12, 1989. In this disclosure, body activity sensors, such as temperature, motion, respiration and/or blood oxygen sensors, are positioned in a patient's body outside a pacer capsule. The sensors wirelessly transmit body activity signals, which are processed by circuitry in the heart pacer. The heart pacing functions are influenced by the processed signals. The signal transmission is a two-way network and allows the sensors to receive control signals for altering the sensor characteristics.

One of the many limitations of Stranberg is the fact that although there is corporeal two-way communications between the implantable medical devices, and the functional response of the heart pacer is processed in the pacer after collecting input from the other sensors, the processor is not remotely programmable. Specifically, the system does not lend itself to web-based communications to enable remote troubleshooting, maintenance and upgrade from outside the patient's body because the processor/programmer is internally located in the patient forming an integral part of the heart pacer.

Yet another prior art reference provides a multi-module medication delivery system as disclosed by Fischell in U.S. Pat. No. 4,494,950 issued Jan. 22, 1985. The disclosure relates to a system consisting a multiplicity of separate modules that collectively perform a useful biomedical purpose. The modules communicate with each other without the use of interconnecting wires. All the modules may be installed intracorporeal or mounted extracorporeal to the patient. In the alternate, some modules may be intracorporeal with others being extracorporeal. Signals are sent from one module to the other by electromagnetic waves. Physiologic sensor measurements sent from a first module cause a second module to perform some function in a closed loop manner. One extracorporeal module can provide electrical power to an intracorporeal module to operate a data transfer unit for transferring data to the external module.

The Fischell disclosure provides modular communication and cooperation between various medication delivery systems. However, the disclosure does not provide an external programmer with remote sensing, remote data management and maintenance of the modules. Further, the system does neither teach nor disclose an external PDM for telemetrically interacting with the IMDs and the programmer.

An additional example of prior art practice includes a packet-based telemedicine system for communicating information between central monitoring stations and a remote patient monitoring station disclosed in Peifer, WO 99/14882 published Mar. 25, 1999. The disclosure relates to a packet-based telemedicine system for communicating video, voice and medical data between a central monitoring station and a patient that is remotely located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combination of network architectures, including a community access television (CATV) network, the public switched telephone network (PSTN), the integrated services digital network (ISDN), the Internet, a local area network (LAN), a wide area network (WAN), over a wireless communications network, or over asynchronous transfer mode (ATM) network. A separate transmission code is not required for each different type of transmission media.

One of the advantages of the Pfeifer invention is that it enables data of various forms to be formatted in a single packet irrespective of the origin or medium of transmission. However, the data transfer system lacks the capability to remotely debug the performance parameters of the medical interface device or the programmer. Further, Pfeifer does not disclose a method or structure by which the devices at the patient monitoring station may be remotely updated, maintained and tuned to enhance performance or correct errors and defects. Specifically, the Pfeifer invention does not disclose a programmer and a PDM co-operatively engaged to manage the regulated and unregulated functions of IMDs to provide efficient and chronic monitoring for real-time delivery of therapy and diagnosis.

Another example of a telemetry system for implantable medical devices is disclosed in Duffin et al, U.S. Pat. No. 5,752,976, issued May 19, 1998, incorporated by reference herein in its entirety. Generally, the Duffin et al disclosure relates to a system and method for communicating with a medical device implanted in an ambulatory patient and for locating the patient in order to selectively monitor device function from a remote medical support network. The communications link between the medical support network and the patient communications control device may comprise a world wide satellite network, a cellular telephone network or other personal communications system.

Although the Duffin et al disclosure provides significant advances over the prior art, it does not teach a communications scheme in which a programmer and a PDM unit interact with IMDs to remotely debug, maintain, upgrade or modify the functional elements of IMDs. Specifically, the Duffin et al disclosure is limited to notifying remote medical support personnel or an operator about impending problems with an IMD and also enables constant monitoring of the patient's position worldwide using the GPS system. However, Duffin et al does not teach the remote monitoring and chronic management of the IMD to dispense therapy and diagnosis as required.

In a related art, Thompson discloses a patient tracking system in a co-pending application entitled "World-wide Patient Location and Data Telemetry System For Implantable Medical Devices", Ser. No. 09/045,272, filed on Mar. 20, 1998 which is incorporated by reference herein in its entirety. The disclosure provides additional features for patient tracking in a mobile environment worldwide via the GPS system. However, the remote programming concepts advanced by the present invention are not within the purview of the Thompson disclosure because there is no teaching of a web-based environment in which a programmer and a PDM unit operate as interactive units of the web-based data, management, therapy and diagnosis system.

Yet in another related art, Ferek-Petric discloses a system for communication with a medical device in a co-pending application, Ser. No. 09/348,506 which is incorporated by reference herein in its entirety. The disclosure relates to a system that enables remote communications with a medical device, such as a programmer. Particularly, the system enables remote communications to inform device experts about programmer status and problems. The experts will then provide guidance and support remotely to service personnel or operators located at the programmer. The system may include a medical device adapted to be implanted into a patient; a server PC communicating with the medical device; the server PC having means for receiving data transmitted across a dispersed data communication pathway, such as the Internet; and a client PC having means for receiving data transmitted across a dispersed communications pathway from the SPC. In certain configurations the server PC may have means for transmitting data across a dispersed data communication pathway (Internet) along a first channel and a second channel; and the client PC may have means for receiving data across a dispersed communication pathway from the server PC along a first channel and a second channel.

One of the significant teachings of Ferek Petric's disclosure, in the context of the present invention, includes the implementation of communication systems, associated with IMDs that are compatible with the Internet. Specifically the disclosure advances the art of remote communications between a medical device, such as a programmer and a PDM unit and experts located at a remote location preferably using the Internet or equivalent network. Primarily, among the many objectives of the invention the communications scheme is structured to alert remote experts to existing or impending problems with the IMDs and/or the programming device so that prudent action, such as early maintenance or other remedial steps, may be timely exercised. Further, because of the early warning or advance knowledge of the problem, the remote expert would be well informed to provide remote advice or guidance to service personnel or operators at the programmer.

While Ferek's invention advances the art in communications systems relating to interacting with a programmer via a communication medium such as the Internet, the system does neither propose nor suggest a programmer and a PDM unit performing specialized tasks remotely to enhance patient therapy and clinical care.

Another disclosure relating to ambulatory patient health monitoring techniques utilizing interactive visual communications is disclosed by Daniel et al in U.S. Pat. No. 5,441,047, issued Aug. 15, 1995. The invention relates to a system in which the patient is monitored by a health care worker at a certain station, while the patient is at a remote location. The patient's condition is monitored in the home using various monitoring devices. The health care worker is placed into interactive visual communication with the patient.

Yet another prior art provides a monitoring method and a monitoring equipment in U.S. Pat. No. 5,840,020 by Pekka et al issued on Nov. 24, 1998. The patent relates to a monitoring equipment including means for receiving a measurement result indicating the patients blood glucose level, and for storing it in memory. In order to improve and facilitate the treatment of the patient, the monitoring equipment further includes means for receiving data concerning the patient's diet, medication and physical strain and for storing it in the memory. A series of calculations are refined to provide predictive values.

Further, another prior art provides a method for monitoring the health of a patient as disclosed in U.S. Pat. No. 5,772,586 issued to Pekka et al on Jun. 30, 1998. The disclosure relates to a method for monitoring the health of a patient by utilizing measurements. In order to improve the contact between the patient and the person treating him, the results of the measurements are supplied via a communications device utilizing a wireless data transmission link to a data processing system available to the person monitoring the patient's health. The patient's health is monitored by means of the data stored in the data processing system.

Yet a further example of a prior art is provided in U.S. Pat. No. 5,701,904 by Simmons et al issued on Dec. 30, 1997 relating to telemedicine instrumentation pack. The invention includes a portable medical diagnostic apparatus for data gathering . A video camera generates signals based on images taken from the visual instruments. Other electronics circuitry generates signals based on output of the audio instrument and data-gathering instruments. The signals are transmitted to a remote site for analysis by medical personnel.

Yet another example of a prior art is provided in U.S. Pat. No. 5,311,449 by Adams relating to sterilization hand-held programmer or interrogator. The patent discloses a unit that communicates with an IMD to function fully as a data programmer and as an interrogator. Interrogated data can be linked directly to the surgeon via a modem. One of the limitations of the Adam patent is the fact that the hand-held unit is a programmer with limited functions. In sharp contrast the present invention relates, inter alia, to a specialized co-operative structure and scheme between a programmer and a PDM unit to share and perform specialized functions to provide a highly mobile and adaptable system for management of IMDs. Significantly, the present invention provides a web-based bi-directional communications system as a data manager to enable delivery of a comprehensive therapy and diagnosis in real time.

Accordingly, it would be advantageous to provide a system in which a programmer and a PDM could uplink to a remote expert data center to import enabling software for monitoring, therapy and diagnosis. Yet another desirable advantage would be to provide a system to implement the use of remote expert systems to manage the operations of IMDs on a real-time basis. A further desirable advantage would be to provide a communications scheme that is compatible with various communications media, to promote a fast uplink of a programmer and a PDM to remote expert systems and specialized data resources. Yet another desirable advantage would be to provide a high speed communications scheme to enable the transmission of high fidelity sound, video and data to advance and implement efficient remote data management of a clinical/therapy system via a programmer and a PDM thereby enhancing patient clinical care. Yet a further desirable advantage would be to simplify the components and cost of a programmer by integrating it with a PDM to thereby enable web-based data management where the PDM is implemented as a data messenger. As discussed herein below, the present invention provides these and other desirable advantages.

SUMMARY OF THE INVENTION

The present invention generally relates to a communications scheme in which a remote web-based expert data center interacts with a patient having one or more implantable medical devices (IMDs) via associated external medical devices, preferably a programmer and a PDM, located in close proximity to the IMDs. Some of the most significant advantages of the invention include the use of various communications media between the remote web-based expert data center and the programmer to remotely exchange clinically significant information and ultimately effect real-time parametric and operational changes as needed.

In the context of the present invention, one of the many aspects of the invention includes a real-time access of a programmer to a remote web-based expert data center, via a communication network, which includes the Internet. The operative structure of the invention includes the remote web-based expert data center, in which an expert system is maintained, having a bi-directional real-time data, sound and video communications with the programmer via a broad range of communication link systems. The programmer is in turn in telemetric communications with the IMDs such that the IMDs may uplink to the programmer or the programmer may down link to the IMDs, as needed. Further, a PDM is used to uplink data from the programmer to the web-based expert data center. Specifically, the PDM could be used as a highly flexible platform that is readily configurable to transfer data from both the programmer and the IMDs. More specifically, the PDM is implemented to effect a highly adaptable feature to the programmer, IMD and web-based expert system.

Yet another context of the invention includes a communications scheme that provides a highly integrated and efficient method and structure of clinical information management in which various networks such as Community access Television, Local area Network (LAN), a wide area network (WAN), Integrated Services Digital Network (ISDN), the Public Switched telephone Network (PSTN), the Internet, a wireless network, an asynchronous transfer mode (ATM) network, a laser wave network, satellite, mobile and other similar networks are implemented to transfer voice, data and video between the remote data center and a programmer. In the preferred embodiment, wireless communications systems, a modem and laser wave systems are illustrated as examples only and should be viewed without limiting the invention to these types of communications alone. Further, in the interest of simplicity, the applicants refer to the various communications system, in relevant parts, as a communication(s) system. However, it should be noted that the communication(s) system, in the context of this invention, are interchangeable and may relate to various schemes of cable, fiber optics, microwave, radio, laser and similar communications or any practical combinations thereof.

Some of the distinguishing features of the present invention include the use of a robust web-based expert data center to manage and tune the operational and functional parameters of an IMD or IMDs via a programmer and a PDM in real-time. The present invention focuses on the remote real-time monitoring and management of the programmer generally and the IMDs particularly. Specifically, a programmer and a PDM co-operate to provide a flexible and scalable data exchange system via the Internet or equivalent communications media. One of the many advantages of the present invention is the ability to chronically monitor IMDs on a proactive basis to promote the patient's well being.

Yet one of the other distinguishing features of the invention includes the use of a highly flexible and adaptable communications scheme to promote continuous and real-time communications between a remote expert data center, a programmer and a PDM associated with a plurality of IMDs. The IMDs are structured to share information intra-corporeally and may interact with the programmer, as a unit. Specifically, the IMDs either jointly or severally can be interrogated to implement or extract clinical information as required. In other words, all of the IMDs may be accessed via one IMD or, in the alternate, each one of the IMDs may be accessed individually. The information collected in this manner may be transferred to the programmer by up linking the IMDs or via the PDM as needed.

The invention provides significant compatibility and scalability to other web-based applications such as telemedicine and emerging web-based technologies such as tele-immersion. For example, the system may be adapted to applications in which a PDM unit may be used to uplink the patient to a remote data center for non-critical information exchange between the IMDs and the remote expert data center. In these and other web-based similar applications the data collected, in the manner and substance of the present invention, may be used as a preliminary screening to identify the problem and evaluate the need for an interactive data exchange to determine further intervention.

More significantly the present enables high mobility and transferability of data between the IMDs and the programmer and, as well, between an expert data center using a PDM unit that is scalable and adaptable. Further, the PDM unit provides a cost advantage by providing a mobile, hand-heldable platform having high flexibility and scalability for software and hardware changes and upgrade. Particularly, the PDM is a cost-effective extension of the programmer and operates as a data messenger between the programmer, the data center and the IMDs.

BRIEF DESCRIPTION OF THE DRAWINGS

The present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DESCRIPTION OF THE PREFERRED EMBODIMENTS

Figure 1:
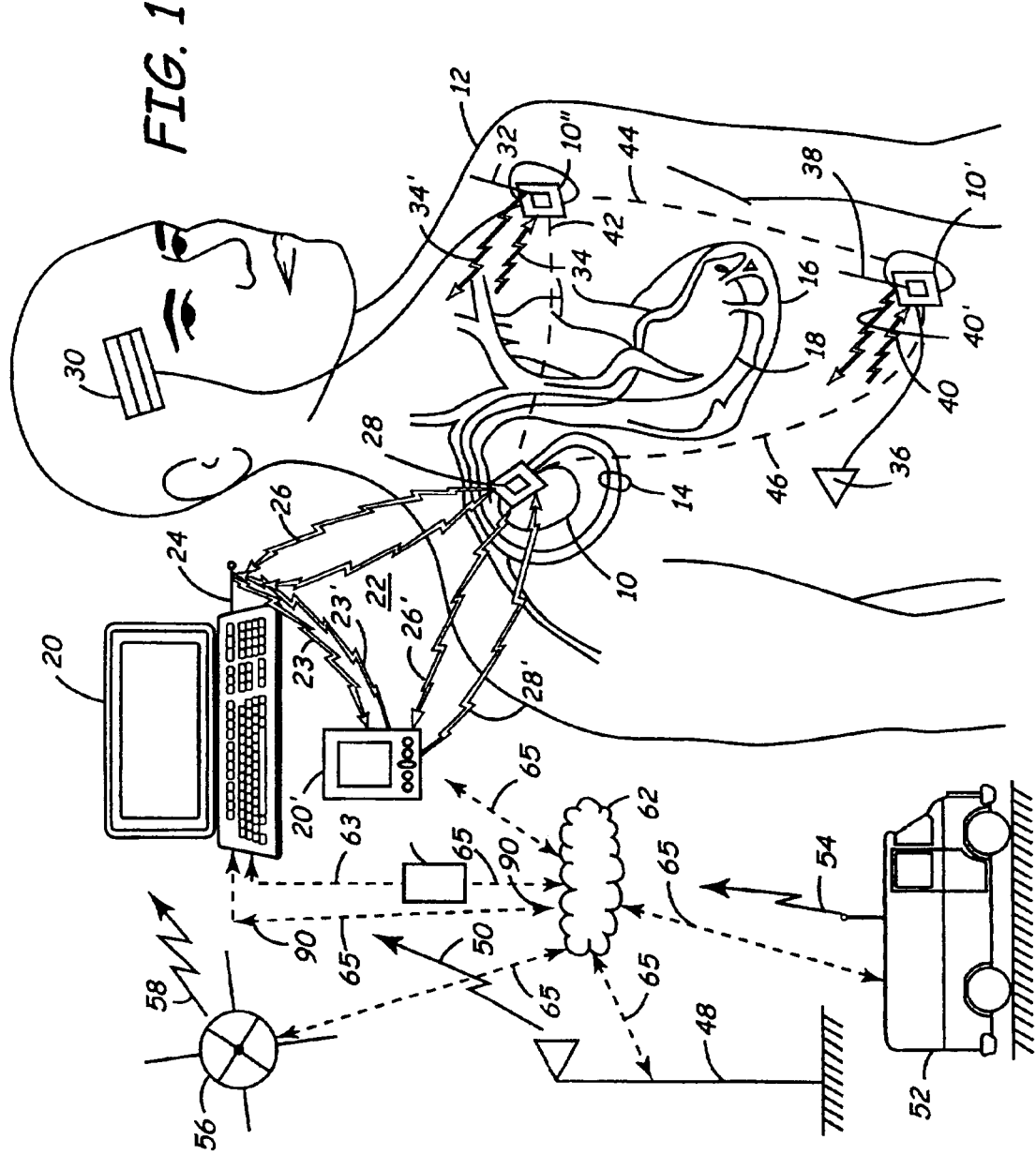
FIG. 1 is a simplified schematic diagram of major uplink and downlink telemetry communications between a remote clinical station, a programmer and a plurality of implantable medical devices (IMDs)

FIG. 1 is a simplified schematic of the major components of the present invention. Specifically, a bi-directional wireless communications system between programmer 20, PDM unit 20' and a number of implantable medical devices (IMDS) represented by IMD 10, IMD 10' and IMD 10" is shown. The IMDs are implanted in patient 12 beneath the skin or muscle. The IMDs are electrically coupled to electrodes 18, 30, and 36 respectively in a manner known in the art. IMD 10 contains a microprocessor for timing, sensing and pacing functions consistent with preset programmed functions. Similarly, IMDs 10' and 10" are microprocessor-based to provide timing and sensing functions to execute the clinical functions for which they are employed. For example, IMD 10' could provide neural stimulation to the brain via electrode 30 and IMD 10" may function as a drug delivery system that is controlled by electrode 36. The various functions of the IMDs are coordinated using wireless telemetry. Wireless links 42, 44 and 46 jointly and severally couple IMDs 10, 10' and 10" such that programmer 20 may transmit commands or data to any or all the of IMDs via one of telemetry antennas 28, 32 and 38. This structure provides a highly flexible and economical wireless communications system between the IMDS. Further, the structure provides a redundant communications system, which enables access to any one of a multiplicity of IMDs in the event of a malfunction of one or two of antennas 28, 32 and 38.

Programming commands or data are transmitted from programmer 20 to IMDs 10, 10' and 10" via external RF telemetry antenna 24. Telemetry antenna 24 may be an RF head or equivalent. Antenna 24 may be located on programmer 20 externally on the case or housing. Telemetry antenna 24 is generally telescoping and may be adjustable on the case of programmer 20. Both programmer 20 and PDM unit 20' may be placed a few feet away from patient 12 and would still be within range to wirelessly communicate with telemetry antennas 28, 32 and 38.

The uplink to remote web-based expert data center 62, hereinafter referred to as, interchangeably, "data center 62", "expert data center 62" or "web-based data center 62" without limitations, is accomplished through programmer 20 or PDM unit 20'. Accordingly programmer 20 and PDM unit 20' function as an interface between IMDs 10, 10' and 10" and data center 62. One of the many distinguishing elements of the present invention includes the use of various scalable, reliable and high-speed wireless communication systems to bi-directionally transmit high fidelity digital/analog data between programmer 20 and data center 62.

There are a variety of wireless mediums through which data communications could be established between programmer 20 or PDM unit 20' and data center 62. The communications link between Programmer 20 or PDM unit 20' and data center 62 could be modem 60, which is connected to programmer 20 on one side at line 63 and data center 62 at line 64 on the other side. In this case, data is transferred from data center 62 to programmer 20 via modem 60. Alternate data transmission systems include, without limitations, stationary microwave and/or RF antennas 48 being wirelessly connected to programmer 20 via tunable frequency wave delineated by line 50. Antenna 48 is in communications with data center 62 via wireless link 65. Similarly, PDM unit 20', mobile vehicle 52 and satellite 56 are in communications with data center 62 via wireless link 65. Further, mobile system 52 and satellite 56 are in wireless communications with programmer 20 or PDM unit 20' via tunable frequency waves 54 and 58, respectively.

In the preferred embodiment a Telnet system is used to wirelessly access data center 62. Telnet emulates a client/server model and requires that the client run a dedicated software to access data center 62. The Telnet scheme envisioned for use with the present invention includes various operating systems including UNIX, Macintosh, and all versions of Windows.

Functionally, an operator at programmer 20 or an operator at data center 62 would initiate remote contact. Programmer 20 is down linkable to IMDs via link antennas 28, 32 and 38 to enable data reception and transmission. For example, an operator or a clinician at data center 62 may downlink to programmer 20 to perform a routine or a scheduled evaluation of programmer 20. In this case the wireless communication is made via wireless link 65. If a downlink is required from programmer 20 to IMD 10 for example, the downlink is effected using telemetry antenna 22. In the alternate, if an uplink is initiated from patient 12 to programmer 20 the uplink is executed via wireless link 26. As discussed herein below, each antenna from the IMDs can be used to uplink all or one of the IMDs to programmer 20. For example, IMD 10" which relates to neural implant 30 can be implemented to up-link, via wireless antenna 34 or wireless antenna 34', any one, two or more IMDs to programmer 20. Preferably bluetooth chips, adopted to function within the body to outside the body and also adopted to provide low current drain or an equivalent chip, are embedded in order to provide wireless and seamless connections 42, 44 and 46 between IMDs 10, 10' and 10". The communication scheme is designed to be broadband compatible and capable of simultaneously supporting multiple information sets and architecture, transmitting at relatively high speed, to provide data, sound and video services on demand.

Figure 2:
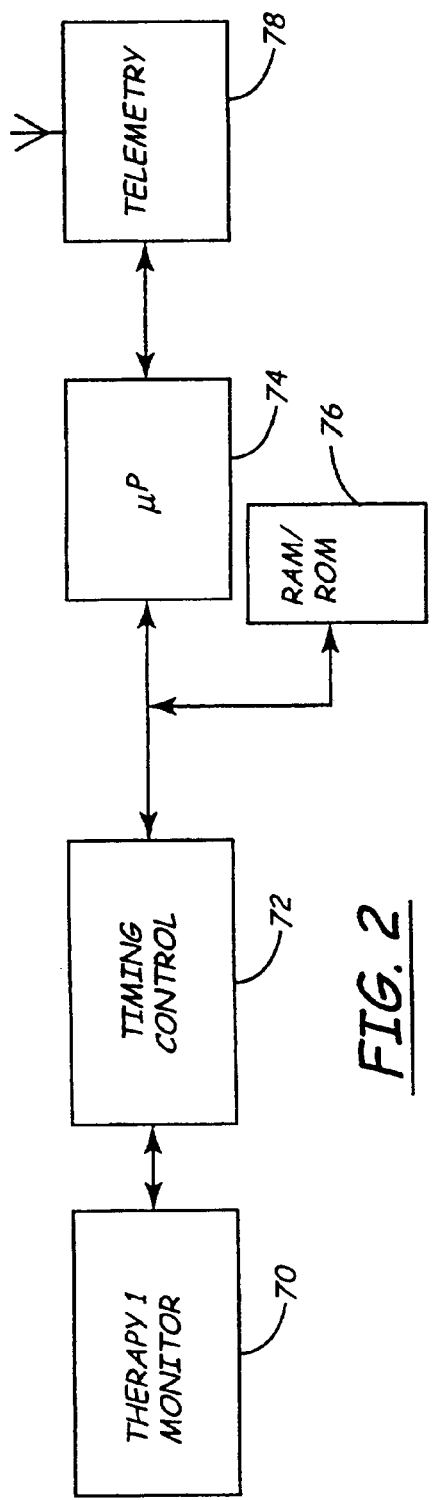
FIG. 2 is a block diagram representing the major components of an IMD.

FIG. 2 illustrates typical components of an IMD, such as those contemplated by the present invention. Specifically, major operative structures common to all IMDs 10, 10' and 10" are represented in a generic format. In the interest of brevity, IMD 10 of FIG. 2 is a representation of all the IMDs and in the context of this disclosure the term IMD or IMD 10 refers to all the IMDs. Accordingly, IMD 10 is implanted in patient 12 beneath the patient's skin or muscle and is electrically coupled to heart 16 of patient 12 through pace/ sense electrodes and lead conductor(s) of at least one cardiac pacing lead 18 in a manner known in the art. IMD 10 contains timing control 72 including operating system that may employ microprocessor 74 or a digital state machine for timing, sensing and pacing functions in accordance with a programmed operating mode. IMD 10 also contains sense amplifiers for detecting cardiac signals, patient activity sensors or other physiologic sensors for sensing the need for cardiac output, and pulse generating output circuits for delivering pacing pulses to at least one heart chamber of heart 16 under control of the operating system in a manner well known in the prior art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry on receipt of a retrieval or interrogation instruction. All of these functions and operations are well known in the art, and many are generally employed to store operating commands and data for controlling device operation and for later retrieval to diagnose device function or patient condition.

Programming commands or data are transmitted between IMD 10, RF telemetry antenna 28, for example, and an external RF telemetry antenna 24 associated with programmer 20. In this case, it is not necessary that the external RF telemetry antenna 24 be contained in a programmer RF head so that it can be located close to the patient's skin overlying IMD10. Instead, the external RF telemetry antenna 24 can be located on the case of programmer 20. It should be noted that programmer 20 can be located some distance away from patient 12 and is locally placed proximate to the IMDs such that the communication between IMDs 10, 10' and 10" and programmer 20 is telemetric. For example, programmer 20 and external RF telemetry antenna 24 may be on a stand a few meters or so away from patient 12. Moreover, patient 12 may be active and could be exercising on a treadmill or the like during an uplink telemetry interrogation of real-time ECG or other physiologic parameters. Programmer 20 may also be designed to universally program existing IMDs that employ RF telemetry antennas of the prior art and therefore also have a conventional programmer RF head and associated software for selective use therewith.

In an uplink communication between IMD 10 and programmer 20, for example, telemetry transmission 22 is activated to operate as a transmitter and external RF telemetry antenna 24 operates as a telemetry receiver. In this manner data and information may be transmitted from IMD 10 to programmer 20. In the alternate, IMD 10 RF telemetry antenna 26 operates as a telemetry receiver antenna to downlink data and information from programmer 20. Both RF telemetry antennas 22 and 26 are coupled to a transceiver comprising a transmitter and a receiver.

Similarly, PDM 20' communicates with programmer 20 via telemetry antennas 23 and 23'. Further, in a specialized application, PDM 20' may communicate with IMDs 10, 10' and 10" via telemetry antennas 26 and 26'. (See FIG. 1)

Figure 3B:
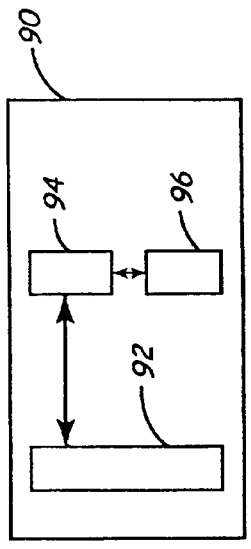
FIG. 3B is a block diagram representing a laser transceiver for high speed transmission of voice, video and other data.
Figure 3A:
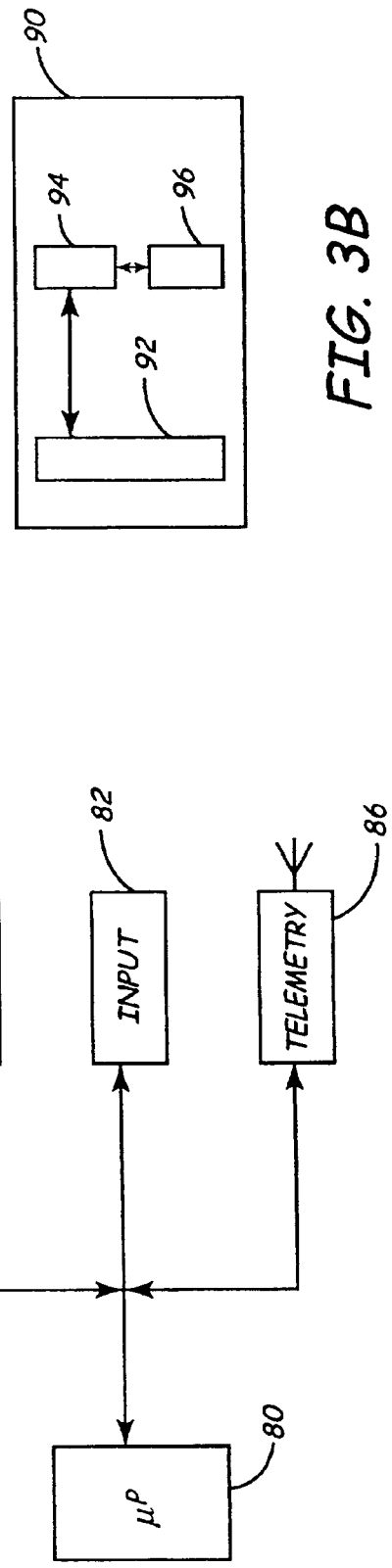
FIG. 3A is a block diagram presenting the major components of a programmer.

FIG. 3A is a simplified circuit block diagram of major functional components of programmer 20. The external RF telemetry antenna 24 on programmer 20 is coupled to a telemetry transceiver 86 and antenna driver circuit board including a telemetry transmitter and telemetry receiver 34. The telemetry transmitter and telemetry receiver are coupled to control circuitry and registers operated under the control of microcomputer 80. Similarly, within IMD 10, for example, the RF telemetry antenna 26 is coupled to a telemetry transceiver comprising a telemetry transmitter and telemetry receiver. The telemetry transmitter and telemetry receiver in IMD 10 are coupled to control circuitry and registers operated under the control of microcomputer 74.

Further referring to FIG. 3A, programmer 20 is a personal computer type, microprocessor-based device incorporating a central processing unit, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Operation of the programmer in accordance with the present invention is controlled by microprocessor 80.

In order for the physician, other caregiver or operator to communicate with the programmer 20, a keyboard or input 82 coupled to CPU 80 is optionally provided. However the primary communications mode may be through graphics display screen of the well-known "touch sensitive" type controlled by a graphics circuit. A user of programmer 20 may interact therewith through the use of a stylus, also coupled to a graphics circuit, which is used to point to various locations on screen or display 84 which display menu choices for selection by the user or an alphanumeric keyboard for entering text or numbers and other symbols. Various touch-screen assemblies are known and commercially available. Display 84 and or the keyboard comprise means for entering command signals from the operator to initiate transmissions of downlink or uplink telemetry and to initiate and control telemetry sessions once a telemetry link with data center 62 or an implanted device has been established. Display screen 84 is also used to display patient related data and menu choices and data entry fields used in entering the data in accordance with the present invention as described below. Display screen 84 also displays a variety of screens of telemetered out data or real-time data. Display screen 84 may also display uplinked event signals as they are received and thereby serve as a means for enabling the operator to timely review link-history and status.

Programmer 20 further comprises an interface module, which includes digital circuit, non-isolated analog circuit, and isolated analog circuit. The digital circuit enables the interface module to communicate with the interface controller module. As indicated hereinabove, the operation of programmer 20, in accordance with the present invention, is controlled by microprocessor 80. Programmer 20 is preferably of the type that is disclosed in U.S. Pat. No. 5,345,362 to Winkler, which is incorporated by reference herein in its entirety.

Screen 84 may also display up-linked event signals when received and thereby serves as a means for enabling the operator of programmer 20 to correlate the receipt of uplink telemetry from an implanted device. Programmer 20 is also provided with a strip chart printer or the like coupled to interface controller module so that a hard copy of a patient's ECG, EGM, marker channel of graphics displayed on the display screen can be generated.

As will be appreciated by those of ordinary skill in the art, it is often desirable to provide a means for programmer 20 to adapt its mode of operation depending upon the type or generation of implanted medical device to be programmed and to be compliant with the wireless communications system through which data and information are transmitted between programmer 20 and data center 62.

FIG. 3B is an illustration of the major components of Wave unit 90 utilizing laser technologies such as for example the WaveStar Optic Air Unit, manufactured by Lucent Technologies or equivalent. This embodiment may be implemented for large data transfer at high speed in applications involving several programmers. The unit includes laser 92, transceiver 94 and amplifier 96. A first wave unit 90 is installed at data center 62 and a second unit 90' is located proximate to programmer 20 or PDM unit 20'. Data transmission between remote data center 62 and programmer unit 20 is executed via wave units 90. Typically, the first wave unit 90 accepts data and splits it into unique wavelength for transmission. The second wave unit 90' recomposes the data back to its original form.

Figure 4:
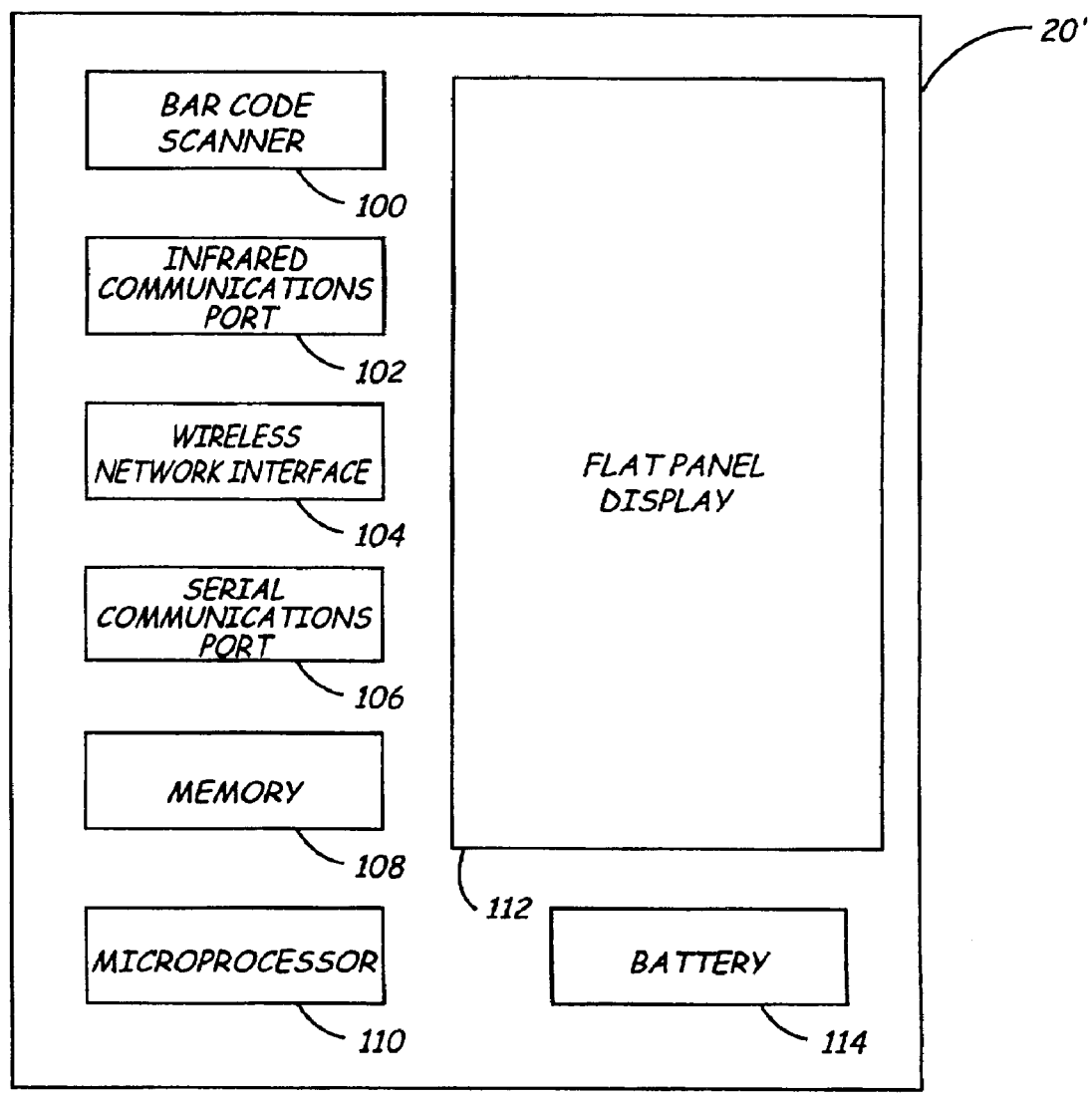
FIG. 4 is a block diagram illustrating the high level functional elements of the PDM.

FIG. 4 is a representation of the major components of PDM 20'. The unit includes bar code scanner 100, infrared communication port 102, wireless network interface 104, serial communications port 106. PDM 20' further includes memory 108, microprocessor 110 and battery/power source 114. Flat panel display 112 is used to enable visual and tactile user interface.

PDM 20' is implemented as a handheld device to primarily transfer data into and out of programmer 20. In yet another embodiment, PDM 20' is used to transfer data to and from both programmer 20 and/or IMD 10. The latter implementation requires that PDM 20' be able to access only the unregulated non-medical environments of IMD 10.

More specifically, PDM 20' is preferably powered via battery 114 and shall interface with programmer 20 via infrared communication port 102 and wireless network interface 104. Data transferred from programmer 20 is stored in memory 108. Barcode scanner 100 is used to read the identification of IMD 10 before implant and is intended to aid in tracking IMD and component inventories. In the preferred embodiment, before implantation, IMD 10 barcode is scanned into PDM 20' and is stored. Thereafter, the identifying barcode is transferred to programmer 20 from PDM 20'. Serial communication port 106 is implemented to exchange data between memory 108 and other computers, servers, etc., adapted with the required hardware and software. Further, wireless network interface 104 is preferably implemented to access networks and the Internet.

Figure 5:
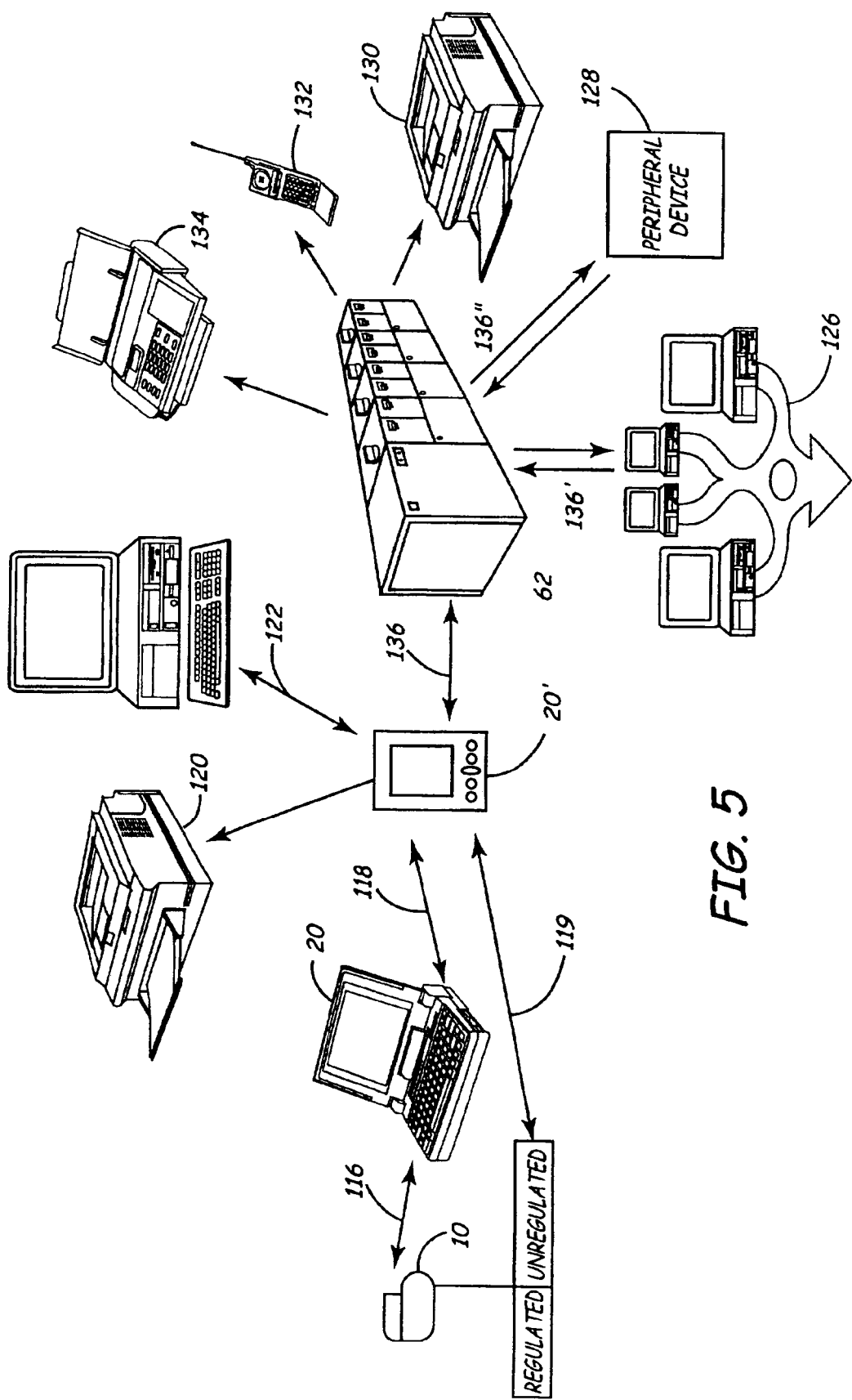
FIG. 5 is a block diagram illustrating the implementation of the PDM in the web-based communications scheme of the present invention.

FIG. 5 is a representative of the bi-directional communication system in which PDM 20' is implemented. PDM 20' is preferably used to carry data from programmer 20. In the preferred embodiment data that is transferred from programmer 20 is printable at printer 120. Further PDM 20' may be used to transfer data from programmer 20 to PC 122 and expert data center 62. As discussed hereinabove, expert data center 62 is a web-based system which is the data/information hub for the remote management of programmer 20 and IMD 10. Data Center 62 is in a bi-directional data communication with fax 134, cellular phone 132, printer 130, peripheral device 128 and LAN or WAN 126.

Programmer 20 is in a bi-directional data communication with IMD 10 via link 116. Similarly, links 118, 136, 136' and 136" represent bi-directional data communications between programmer 20 and PDM 20', data center 136 and PDM 20', data center 62 and LAN/WAN 126, and data center 62 and peripheral device 128, respectively.

In yet another preferred embodiment, PDM 20' may be adopted to directly interact with IMD 10 to transfer data to and from IMD 10 within the unregulated portion of the data and operations regime. In this manner unregulated aspects of IMD 10 could be programmed, modified or changed via PDM 10. Further, the unregulated data and operation of IMD 10 could be directly transferred to, for example, data center 62 by using PDM 20' as a data messenger thus by-passing programmer 20.

Figure 6A:
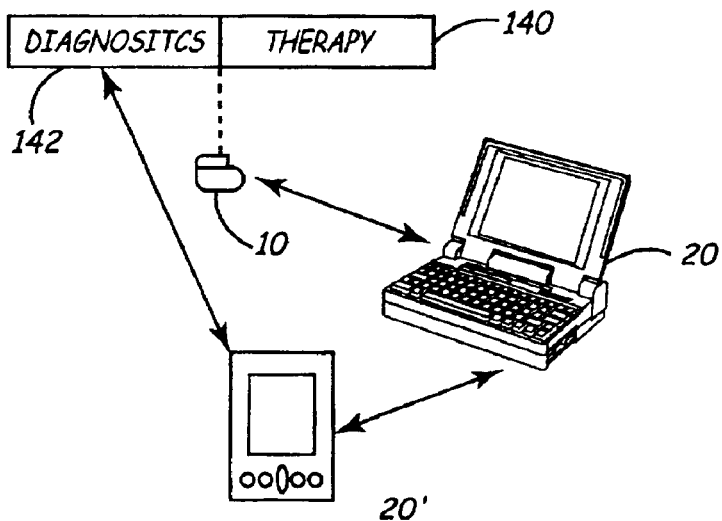
FIG. 6A represents a bi-directional communications scheme between the PDM, a programmer and an IMD.
Figure 6B:
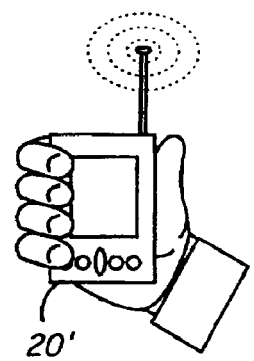
FIG. 6B represents the independent use of the PDM used as a messenger.
Figure 6C:
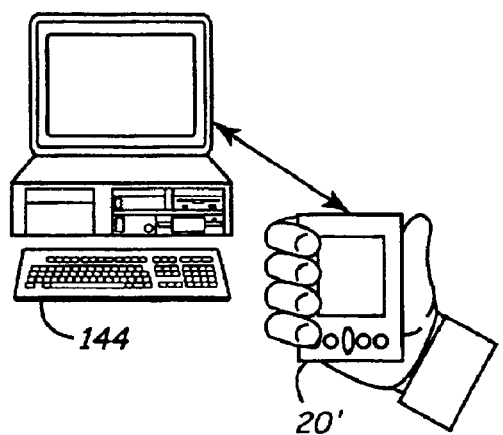
FIG. 6C represents the PDM being implemented in a bi-directional communications with a PC or computer system.

FIG. 6A depicts an embodiment in which PDM 20' is implemented to communicate with programmer 20 and to a non-restricted portion of IMD 10. Under normal conditions, PDM 20' is uplinked to programmer 20 to transfer data to data center 62. In this capacity, PDM 20' is used as a mobile data messenger (see FIG. 6B). PDM 20' may also be brought in data communications with PC 144 (see FIG. 6C) or printer 146 (see FIG. 6C).

Figure 6D:
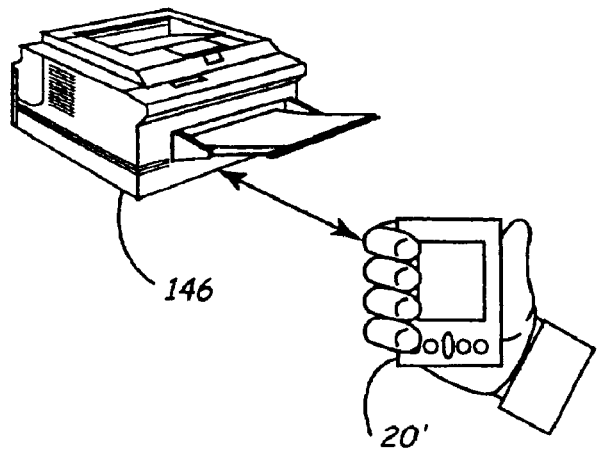
FIG. 6D represents the PDM being implemented in a bi-directional communications with a printer.

Referring to FIG. 6A further, PDM 20' is used as a medical messenger to store and forward data to and from a medical environment through infra red communications port 102. Further, in accordance with FIG. 6B, PDM 20' is implemented as a medical messenger to store and forward data from remote data center 62 through wireless network 104. Similarly, in accordance with FIG. 6C, PDM 20' is implemented to store and forward information to and from PC 144 or to a network of PC's (not shown). Any of PDM 20' data ports could be used to effect these data exchanges. Additionally, in accordance with FIG. 6D, PDM 20' could be used to transfer information from a medical environment to printer 146 or similar device.

As applied herein, the medical environment includes IMD 10, programmer 20 and the remote data center 62 in which PDM 20' is implemented. Specifically, the medical environment implies a network of medical devices integrated to provide clinical therapy and diagnosis in real time through the exchange of pertinent data. PDM 20', of the present invention, facilitates the transfer and exchange of the data.

Referring to programmer 20 in more detail, when a physician or an operator needs to interact with programmer 20, a keyboard coupled to Processor 80 is optionally employed. However the primary communication mode may be through graphics display screen of the well-known "touch sensitive" type controlled by graphics circuit. A user of programmer 20 may interact therewith through the use of a stylus also coupled to a graphics circuit, which is used to point to various locations on screen/display to display menu choices for selection by the user or an alphanumeric keyboard for entering text or numbers and other symbols as shown in U.S. Pat. No. 5,345,362 incorporated herein in its entirety by reference. Various touch-screen assemblies are known and commercially available. The display and or the keyboard of programmer 20, preferably include means for entering command signals from the operator to initiate transmissions of downlink-telemetry from IMDs and to initiate and control telemetry sessions once a telemetry link with one or more IMDs has been established. The graphics display /screen is also used to display patient related data and menu choices and data entry fields used in entering the data in accordance with the present invention as described below. The graphics display/screen also displays a variety of screens of telemetered out data or real-time data. Programmer 20 is also provided with a strip chart printer 118 or the like coupled to interface controller module so that a hard copy of a patient's ECG, EGM, marker channel or similar graphics display can be generated. Further, Programmer 20's history relating to instrumentation and software status may be printed from printer. Similarly, once an uplink is established between programmer 20 and any one of IMDs 10, 10' and 10", various patient history and IMD performance data may be printed out. The IMDs contemplated by the present invention include a cardiac pacemaker, a defibrillator, a pacer-defibrillator, implantable monitor (Reveal), cardiac assist device, and similar implantable devices for cardiac rhythm and therapy. Further the IMD units contemplated by the present invention include electrical stimulators such as, but not limited to, a drug delivery system, a neural stimulator, a neural implant, a nerve or muscle stimulator or any other implant designed to provide physiologic assistance or clinical therapy.

Expert data center 62 represents a high speed computer network system which is located remotely, with respect to the IMDs, having wireless bi-directional data, voice and video communications with programmer 20 via wireless communications link 116 (See FIG. 5). Generally data center 62 is preferably located in a central location and is equipped with high-speed web-based computer networks. Preferably, the data resource center is manned 24-hours by operators and clinical personnel who are trained to provide a web-based remote service to programmer 20. Additionally, as discussed hereinabove, data resources 62 provide remote monitoring, maintenance and upgrade of programmer 20. The location of data center 62 is dependent upon the sphere of service. In accordance with the present invention, data resource 62 may be located in a corporate headquarters or manufacturing plant of the company that manufactures programmer 20. Wireless data communications link/connection 116 can be one of a variety of links or interfaces, such as a local area network (LAN), an internet connection, a telephone line connection, a satellite connection, a global positioning system (GPS) connection, a cellular connection, a laser wave generator system, any combination thereof, or equivalent data communications links.

As stated hereinabove, bi-directional wireless communications 116 acts as a direct conduit for exchange of information between data center 62 and programmer 20. Further, bi-directional wireless communications 118 provides an indirect link between data center 62 and IMDS 10, 10' and 10" via PDM 20'. Similarly, bi-directional communication links 136' and 136" represent a data, voice, and/or video communications between data center 62 and LAN/WAN 126 and peripheral device 128, respectively.

As discussed above, programmer 20 is a medical device which is coupled to IMD 10 via lead 18. IMDs 10, 10' 10" represent various implantable medical devices, such as cardiac pacemakers, defibrillators, pacemaker/defibrillators, and combinations thereof. Further, IMDs 10, 10' and 10" may represent drug delivery systems, electrical stimulators including nerve and muscle stimulators, deep brain stimulators, or heart assist devices or pumps.

Programmer 20 enables the operator to assess the performance of IMD 10 and its associated circuitry via information link 116. Specifically, procedures involving implantation of IMD 10, programming of IMD 10, and transmission of operational information feedback from IMD 10 are controlled and monitored by programmer 20. These procedural functions are checked by an operator who manages the various functions of programmer 20. Programmer 20 includes software applications for monitoring the IMDs.

In the context of the present invention, PDM 20' is a strategic tool which is mobile and could be used as a highly adaptable platform for implementing a variety of software to manage the unregulated aspects of the IMDs. Specifically, PDM 20' is implemented as a support platform for programmer 20 by being a specialized highly functional store-foreward data manager. PDM 20' is handheldable and offers high mobility. Further, PDM 20' is readily adaptable to both hardware and software changes. This feature makes the PDM 20' an effective complementary tool for data upgrade, and means of transfer/exchange of data complementing programmer 20 and IMD 10, in a cost effective manner.

Accordingly, the present invention provides inter alia, a remote handheldable manager and data exchange unit to work with programmers worldwide. Generally, in the context of the invention, all programmers located proximate to IMDs or patients with IMDs and distributed globally are connected to an expert data center to share software upgrades and access archived data. The programmer and the PDM of the present invention function as an interface between the remotely located expert data center and the IMDs. Further, procedural functions such as monitoring the performance of the IMDs, upgrading software in the IMDs, upkeep and maintenance of the IMDS and related functions are implemented via the programmer and the PDM. The preferably telemetric and yet local interaction between the programmer, the PDM and the IMDs enable delivery of therapy and clinical care in real time. In order to facilitate the just-in-time patient care at the location of the patient, the invention provides a highly efficient data exchange/data transfer system. This scheme enables the dissemination of software and clinical data worldwide while maintaining a high standard of patient care at reduced costs.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. A method for remotely conducting interactive patient diagnostics for a patient having one or more implantable medical devices (IMDs), monitoring the patient, and delivering therapy to the patient, all of which is carried out over a bi-directional communication system establishing a communications network link and comprising a remote web-based expert data center, a programmer for the IMDs, and a hand-held personal data monitor (PDM) operating as an interface to the programmer, the method comprising the steps of:

connecting the programmer to the remote data center for data communication via the data communications network link;

connecting the PDM to the programmer and transferring data into and out of the programmer with the PDM; and uplinking data from the IMD to the programmer.

2. The method of claim 1, further comprising the step of connecting the PDM to the IMD.

3. The method of claim 2, wherein the data communications network is an intranet.

4. The method of claim 1, further comprising the step of using the PDM to transfer data messenger between the IMD, the remote data center and the programmer.

5. The method of claim 4, further comprising the step of using the PDM to transfer pre-implant data to the programmer.

6. The method of claim 4, further comprising the step of using the PDM to modify, store and forward data for use in an unregulated section of the programmer.

7. The method of claim 1, further comprising the step of using the PDM to secure an identity of the IMD before implant.

8. The method of claim 1, wherein the data communications network is an internet.

9. The method of claim 1, wherein the data communications network further includes a satellite.

10. The method of claim 1, wherein the communications network further includes a telephone line.

11. The method of claim 1, wherein the data communications network further includes a global positioning system.

12. The method of claim 1, wherein the data communications network includes at least two communication links selected from the group of communication links consisting of a telephone line, an intranet, an internet, a satellite, a laser wave form, and a global positioning system.

13. The method of claim 1, wherein the PDM operates in real time data transmission using data packets routed to the remote data center through a high speed wireless network interface coupled to the PDM.

14. The method of claim 1, wherein the PDM operates in real time data transmission using data packets routed to the remote data center through a serial port coupled to the PDM.

15. The method of claim 14, further comprising the step of connecting the serial port to a modern.

16. The method of claim 1, further comprising the step of using the PDM to store and forward data to and from a personal computer (PC).

17. The method of claim 1, further comprising the step of using the PDM to store and forward information to a printer.

* * * * *